United States Patent [19]

Di Ianni

[11] Patent Number: 4,916,061

[45] Date of Patent: Apr. 10, 1990

[54] GRAM STAINING METHOD AND KIT

[75] Inventor: Ludmilla P. Di Ianni, Hawthorne, N.J.

[73] Assignee: Fisher Scientific Company, Pittsburgh, Pa.

[21] Appl. No.: 132,604

[22] Filed: Dec. 14, 1987

[51] Int. Cl.[4] .............................................. C12Q 1/04
[52] U.S. Cl. .......................................... 435/34; 435/4; 435/29; 435/810; 424/3
[58] Field of Search ...................... 435/29, 34, 810, 36, 435/38; 436/63, 164; 424/3; 8/94.11

[56] References Cited

FOREIGN PATENT DOCUMENTS 0020198  2/1983  Japan .

OTHER PUBLICATIONS

Product Literature, "BBL Differential Gram Stain Reagents" BBL Microbiology Systems, Becton Dickinson & Co. (Apr. 1982).

Hans-Uwe Schenck et al., "Structure of Polyvinylpyrrolidone-Iodine (Povidone-Iodine), " J. Pharmaceutical Sciences, vol. 68, No. 12 (Dec., 1979).

David J. Brigati, workshop publication "Automation and the Future of Histotechnology" (Mar. 7, 1987).

*Primary Examiner*—Robert J. Warden
*Assistant Examiner*—Toni R. Scheiner
*Attorney, Agent, or Firm*—Alan M. Doernberg

[57] ABSTRACT

The present invention provides Gram staining methods and kits in which conventional aqueous iodine-iodide solutions and separate decolorizer solutions are replaced by storage stable alcoholic solutions of iodine-iodide.

15 Claims, No Drawings

GRAM STAINING METHOD AND KIT

BACKGROUND OF THE INVENTION

The present invention relates to Gram staining methods, and kits of reagents therefore.

Conventional Gram staining technique subjects the sample (frequently a specimen which has been smeared on a glass slide and dried) to four solutions in sequence:

(1) aqueous Gentian Violet (also called Crystal Violet, Hexamethyl Violet C.I. No. 42555),
(2) aqueous iodine-iodide (conventionally KI and $I_2$ in water),
(3) decolorizer (conventionally acetone admixed with ethanol or isopropanol), and
(4) counterstain (conventionally Safranin solution).

Handling of the iodine-iodide solution has been improved by the use of polyvinylpyrrolidone-iodine. Theories about how this technique distinguishes Gram Positive from Gram Negative bacteria have varied, but it is often stated that iodine forms a complex with Gentian Violet that is trapped by a barrier in Gram Positive cells that have been dehydrated and treated with mordant and iodine. In Gram Negative bacteria, the barrier is more penetrable, so that the solvent (decolorizer) extracts the iodine-Gentian Violet complex. Thus, it is a common recommendation to leave the iodine solution on the slide for at least one minute and then remove it by gently rinsing with cold tap water before introducing the decolorizer.

BRIEF DESCRIPTION OF THE INVENTION

It has been found that the aqueous iodine-iodide solution and decolorizer solution used in conventional Gram staining can be replaced by a single solution of iodine-iodide in an alcohol. This change permits less steps and also facilitates handling of the iodine-containing reagent.

The invention thus provides a method for the staining of a biological specimen to identify Gram Positive bacteria, which comprises:

(a) staining the biological specimen with Gentain Violet, and
(b) contacting the Gentain Violet stained specimen with a solution comprising iodine, an iodide salt and an alcohol solvent for a time sufficient to intensify the staining of Gram Positive bacteria and to decolorize Gram Negative bacteria.

Preferably, the contacting step (b) is followed by:

(c) counterstaining Gram Negative bacteria in the specimen with a Safranin solution.

The invention further provides a Gram staining kit which comprises:

(a) an aqueous Gentian Violet solution, and
(b) an alcoholic solution of iodine and an iodide salt.

Preferably, the kit further comprises:

(c) an aqueous Safranin solution.

DETAILED DESCRIPTION OF THE INVENTION

The aqueous Gentian Violet solution used in the present method and kit and the aqueous Safranin solution used in the present method and kit can be of conventional composition. Each may contain, in addition to water and the stain, one or more minor components, and especially organic co-solvents (e.g., 1.2 g Crystal Violet, 10 ml isopropanol, 2 g aniline in 100 ml solution with the balance water). The Safranin solution, particularly, can be stain (Safranin-0) at low concentration (e.g., 10 g/L) in water.

The alcoholic iodine-iodide solution preferably has three ingredients: alcohol solvent, elemental iodine and an iodide salt. The alcohol solvent can be any lower alcohol (e.g., methanol, ethanol, isopropanol, n-propanol, t-butanol), but is preferably ethanol. So long as the alcohol is the major component of the solvent, other miscible liquids (and especially water) may be present. It is preferred, however, to have low water content, such as in the 19:1 ethanol:water ratio found in the ethanol-water azeotrope (95% ethanol).

Iodine may be present in the alcohol solvent at any concentration up to the solubility limit, but it is preferred to use a controlled amount that has minimal iodine vapor pressure at room temperature (e.g., 1–5 g/L in 95% ethanol). Various inorganic iodide salts may be used, with NaI and KI being preferred because of the ready availability, and KI being especially preferred because of its conventional use in aqueous iodine-iodide solutions used for Gram staining. The iodide salt can be present up to its solubility limits in the solvent, with concentrations of 3–20 g/L being generally preferred. Overall, the molar ratio of $I_2$ to $I^-$ is not critical, but is preferably 1–3.

A representation formulation used below in Example 1 is:

| | | |
|---|---|---|
| KI | 6.6 g/L | (solid) |
| $I_2$ | 3.3 g/L | (solid) |
| 95% ethanol balance. | | |

It should be appreciated that $I^-$ can be converted in situ to $I_2$ with coventional oxidants, or $I_2$ reduced in situ of $I^-$ with conventional reductants; however, it is generally more convenient to introduce iodine and iodide salt separately. Iodine complexes can be used, but are not preferred.

In using such solution in the present method, one begins with dehydrated tissue in the conventional manner. Thus a thin, uniform smear is prepared on a microscope slide of specimen material from a culture or other source. Water is removed by air drying followed by heating the slide, or by the use of a dehydrating agent.

The dried specimen is then stained with Gentian Violet (Crystal Violet) solution in the conventional manner. For example, each slide can be flooded with the solution for one minute, and then washed gently with cold water. The alcoholic iodine-iodide solution is then applied, preferably first to rinse off water and then to flood the slide. It is also left on the slide for a minute or longer.

At this point, several possible routes can be taken. First, one can then apply a traditional decolorizer solution to assure that the Gentian Violet is fully removed from Gram Negative bacteria. Then, if desired, the Safranin counterstain can be applied. Second, one can proceed directly to washing the slide (for viewing Gram positive bacteria only) or to washing and counterstaining (for viewing Gram Positive and Gram Negative bacteria).

Certain benefits are obtained whether or not the separate decolorizer solution (and step) are omitted. First the iodine solution in alcohol has a much lower iodine vapor pressure than in aqueous iodine-iodide solutions. This prevents loss of iodine activity. Similar results are presently achieved by the use of polyvinylpyrrolidone-iodine complex (Povidone-Iodine) in water.

Certain benefits, however, are obtained in the embodiments of the present invention wherein no separate decolorization solution (or step) is employed. These involve, principally, the savings of time and materials. Additionally, the flammability of acetone-alcohol mixtures places restrictions upon shipment of certain conventional decolorizers that are avoided in some embodiments of the present invention.

The kit of the present invention can be packaged in a variety of ways. Presently, the iodine vapor pressure of aqueous iodine-iodide solutions places severe restrictions upon what type of container can be used. Thus, if such aqueous solutions were packaged in polyethylene, the iodine would permeate the polyethylene container walls and escape. Thus, after a storage period of three weeks, an effective iodine concentration would be lost. By contrast, the present alcohol-based iodine solutions can be stored in polyethylene containers for up to two months at 37° C. without detectable loss of iodine by thiosulfate titration.

EXAMPLE

A two liter solution was prepared from 13.2 g solid KI, 6.6 g solid iodine and two liters of 95% ethanol. Standard microscope slides, on which various bacteria (*S. Aureus, S. Epidermis, E. Coli,* or *Pseudomona Aeruginosa*) were pre-coated, were stained with a standard Gentian Violet solution (Crystal Violet, isopropanol, anilinie, water) and washed gently with cold water.

At this point, some of each group of slides were flooded with the above aqueous KI/iodine solution. After one minute, the slides were rinsed with cold water. Then they were treated with standard aqueous Safranin solution.

In such tests, the *S. Aureus* and *S. Epidermis* slides tested positive, showing the same violet staining of the Gram Positive bacteria as similar slides treated with aqueous KI/iodine and then decolorizer. The *E. Coli* and *Pseudomona Aeruginosa* slides tested negative with alcoholic KI/iodine solution used, with the Gram Negative bacteria appearing pink-red with the Safranin counterstain.

I claim:

1. A method for the staining of a biological specimen to identify Gram Positive bacteria, which comprises:
   (a) staining the biological specimen with Gentian Violet, and
   (b) contacting the Gentian Violet stained specimen with a solution comprising iodine, an iodide salt and an alcohol solvent for a time sufficent to intensify the staining of Gram Positive bacteria and to decolorize Gram Negative bacteria.

2. The method of claim 1 wherein the iodide salt is an alkali metal iodide.

3. The method of claim 1 wherein the iodide salt is potassium iodide.

4. The method of claim 3 wherein the alcohol solvent comprises ethanol.

5. The method of claim 3 wherein the alcohol solvent is 95% ethanol and 5% water.

6. The method of claim 2 wherein the alcohol solvent comprises ethanol.

7. The method of claim 1 wherein the alcohol solvent comprises ethanol.

8. The method of claim 1 further comprising the step:
   (c) counterstaining Gram Negative bacteria in the sample with a Safranin solution.

9. A Gram staining kit which comprises:
   (a) an aqueous Gentian Violet solution in a first container, and
   (b) an alcoholic solution of iodine and an iodide salt in a second container.

10. The kit of claim 9 wherein the iodide salt is an alkali metal iodide.

11. The kit of claim 9 wherein the iodide salt is potassium iodide.

12. The kit of claim 11 wherein the alcoholic solution comprises ethanol, iodine and potassium iodide.

13. The kit of claim 11 wherein the alcoholic solution comprises ethanol and water at a 19:1 weight ratio.

14. The kit of claim 9 wherein the alcoholic solution comprise ethanol, iodine and alkali metal iodide.

15. The kit of claim 9 further comprising:
   (c) an aqueous Safranin solution in a third container.

* * * * *